US006905508B2

(12) United States Patent
Cuccia

(10) Patent No.: US 6,905,508 B2
(45) Date of Patent: Jun. 14, 2005

(54) LUMBAR SUPPORT AND ADJUSTMENT ASSEMBLY

(76) Inventor: David F. Cuccia, 227 Jackson Ave., Syosset, NY (US) 11791

( * ) Notice: Subject to any disclaimer, the term of this patent is extended or adjusted under 35 U.S.C. 154(b) by 105 days.

(21) Appl. No.: 10/410,970

(22) Filed: Apr. 10, 2003

(65) Prior Publication Data

US 2003/0216781 A1 Nov. 20, 2003

Related U.S. Application Data

(63) Continuation-in-part of application No. 09/661,078, filed on Sep. 13, 2000, now Pat. No. 6,547,809.

(51) Int. Cl.[7] ................................................. A61F 5/00
(52) U.S. Cl. ........................ 606/242; 606/241; 606/244
(58) Field of Search ................................ 606/237, 241, 606/242, 243, 244, 245; 602/32, 33, 34, 35, 36; 5/662, 658; 482/142, 112, 113; 128/845; 601/23, 24, 26

(56) References Cited

U.S. PATENT DOCUMENTS

| | | | | | |
|---|---|---|---|---|---|
| 4,582,311 | A | * | 4/1986 | Steffensmeier | 5/614 |
| 4,726,358 | A | * | 2/1988 | Brady | 606/243 |
| 5,176,706 | A | * | 1/1993 | Lee | 606/237 |
| 5,181,904 | A | * | 1/1993 | Cook et al. | 602/32 |
| 5,423,861 | A | * | 6/1995 | Kelley | 606/241 |
| 5,840,001 | A | * | 11/1998 | Schedel | 482/142 |
| 5,860,899 | A | * | 1/1999 | Rassman | 482/142 |
| 5,922,011 | A | * | 7/1999 | Cuccia | 606/241 |
| 6,135,552 | A | * | 10/2000 | Waguri | 128/845 |
| 6,547,809 | B1 | * | 4/2003 | Cuccia | 606/242 |

* cited by examiner

*Primary Examiner*—Danton D. DeMille
*Assistant Examiner*—Quang D. Thanh
(74) *Attorney, Agent, or Firm*—Melvin K. Silverman

(57) ABSTRACT

A rotatable chiropractic treatment table for extension, flexion, traction, distraction and lateral movement of the spine of a patient includes a base adapted to rest upon a floor, and a system support assembly having an upper end and a lower end integrally secured to the base, the support assembly including a pivot axis proximal to upper end. The treatment table also includes a selectable reciprocal extension element having an upper end and a lower end, one end pivotally attached to the system support assembly, the selectable extension elements providing reciprocal movement of the one end relative to an opposite end. The table further includes a rigid support platform having an upper end and a lower end, the platform pivotally secured to the pivot axis of the support assembly and, further, pivotally secured to the one end of the selectable extension element to provide a resultant rotational motion of the support platform. The treatment table yet further includes a body support assembly adjustably positionable relative to the rigid support platform, the assembly having an upper end and a lower end; and an assembly for enabling the patient to remain on the body support assembly during rotational movement.

3 Claims, 9 Drawing Sheets

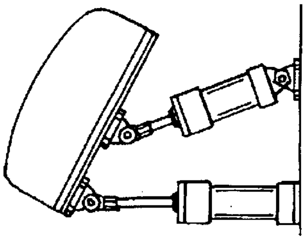
FIG.13
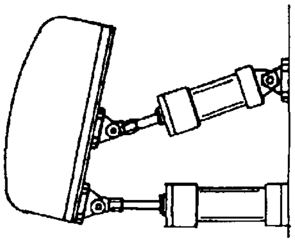
FIG.10
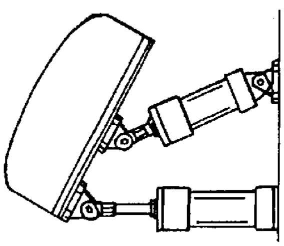
FIG.9
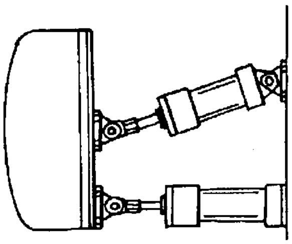
FIG.12
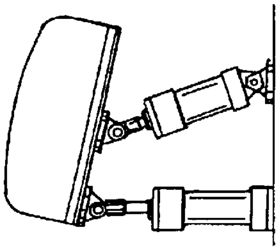
FIG.11
FIG.15
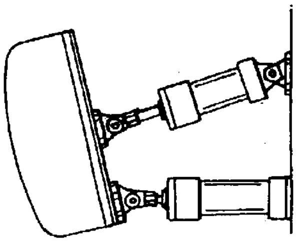
FIG.14
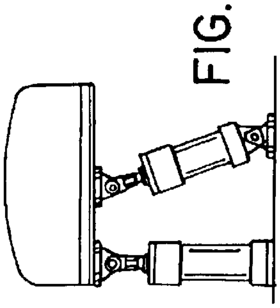

LUMBAR SUPPORT AND ADJUSTMENT ASSEMBLY

REFERENCE TO RELATED APPLICATION

This application is a continuation-in-part of application Ser. No. 09/661,078, filed Sep. 13, 2000 now U.S. Pat. No. 6,547,809, entitled Multi Function Treatment Table.

BACKGROUND OF THE INVENTION

The within invention is an improvement of the inventions of my U.S. Pat. No. 4,915,101 (1990), U.S. Pat. No. 5,922,011 (1999), and that reflected in my application Ser. No. 09/661,078, filed Sep. 13, 2000.

Numerous devices, including chiropractic, osteopathic, obstetrical, delivery, x-ray and operating tables, which suspend or position a patient in a unique way for some special purpose, are known in the art.

U.S. Pat. No. 4,568,669 (1971) to Stiles discloses a posture board wherein the patient is rotated 180 degrees from an initial upright position on his back to one of complete inversion hanging by the ankles. With the body hanging freely, normal gravitational pull is reversed thus causing a therapeutic effect on bone structure, spinal column, muscles, internal organs and body fluids.

U.S. Pat. No. 4,103,681 (1978) to Shanley similarly discloses a tilting traction apparatus where the patient, again lying on his back, is rotated about a pivot point to treat back injury or postural misalignment.

U.S. Pat. No. 4,292,926 (1981) to Krause presents an apparatus for effecting postural treatment of humans in which the patient, while resting face down on a pivoting platform, can vary the position of his arms, adjust his center of gravity while in suspension and, thereby, affect his posture upon the table.

It is to be appreciated that the success of any device designated to treat lower back dysfunction is in large part dependent on proper positioning of the patient prior to, during, and after treatment. For example, in standard traction therapy, the patient wears a pelvic harness and is positioned supinely (face up) in bed, with the spine slightly flexed and knees bent. Straps or roping which is attached to the harness are then inserted into a pulley mechanism and weights attached at an opposite end, causing a desired pulling/traction effect. Such pulling traction force produces an elongation of the spinal column (distraction) and a reduction in internal intervertebral disc pressure. This creates a vacuum phenomenon inside the disc, which retracts protruded gelatinous material back into its fibrous casing and off of the spinal nerve roots. With the pain gone and the anatomy restored to its natural state, the traction phase of therapy is complete.

An alternate theory for accomplishing the same result is based on extension, rather than flexion of the spine, to achieve reduced intradiscal pressure, while simultaneously anatomically moving nerve roots away from the herniated disc.

While the general principles of flexion and axial traction of the spine are known in the art and have been effected in various strap and/or harness arrangements, either alone or in combination with rotating-pivot type tables as are described above, the inventor has found that both flexion and extension, as well as lateral positioning with traction, can all be beneficial depending upon the patient's particular ailment or condition.

As such, there exists a need for a system which combines varying degrees of both traction or distraction with concomitant patient position flexion, extension, lateral flexion, and or axial spinal positioning. The present invention being both beneficial to the patient and convenient to the doctor, fulfills this need in a variety of ways in that the inventive treatment table not only enables rotation of a patient about a pivot point but, additionally, permits the relative, selectable positioning of the patient's arms, upper torso, legs, lower back, head and shoulders through manual adjustment or an automatic keypad control. The present invention also allows a complete choice as to prone, supine or lateral positioning of the patient prior to treatment. It further enables the doctor to vary the position of the patient prior to and during treatment, and to vary the degree of tractive force applied to the patient by selectably variably rotating the patient platform to increase or decrease the tractional gravitational pull applied through such rotation. There is further provided a "dynamic rotation" into a variable vertical traction position, i.e., the patient stands upright against the table, supported by an adjustable shoulder, arm and hand support and is lifted off the ground, thereby achieving tractional dynamics related to those described above, namely a rapid lengthening of the muscles and longitudinal ligaments of the spine increasing the separation of the intervertebral disc and articular joint spaces. This results in both mobilization of the spine and rapid development through the "disc unloading" of a negative internal disc pressure responsible for causing the vacuum phenomenon for retracting protruding disc material back within the borders of a healthy disc while keeping the patient suspended in mid-air, or while the patient remains standing on a weighted patient platform, utilizing the weight of the lower extremity, the force of gravity, and selected patient anatomical positioning.

My instant invention therefore defines functionally over the structure of my earlier inventions in the following material respects:

1. Ability to concurrently or sequentially lift and rotate the patient, thus providing various treatment options to the physician, including more effective traction of vertebral segments prior to and during table and patient rotation, thereby reducing stress on articulate vertebral surfaces of the patient and obtaining a generally more ergonomic patient interface.

2. Ability to change radius of lower back support assembly, to effectuate varying degrees of lumbar extension and lumbar support, as well as a general mobilization of the lumbar spine (lower back).

3. Ability to tilt, at a variety of angles, the top or bottom half of the lower back support assembly, allowing a greater range of positions of the patient's lumbar spine, and to increase or decrease the lumbar lordosis.

SUMMARY OF THE INVENTION

In multi-function chiropractic treatment table, a lumbar support and adjustment assembly includes a rigid support plate mounted upon a rigid body support frame of said table; an upper pneumatic cylinder having an upper piston rod associated therewith, said cylinder having a proximal end rigidly secured to said support frame and having a distal end having an aperture for fluid type reciprocal receipt of a proximal end of said piston rod therein, said piston rod also having a distal end and a lower pneumatic cylinder having a lower piston rod associated therewith, said lower cylinder having a proximal end pivotally secured to said support frame and having a distal end having an aperture for fluid tight reciprocal receipt of a proximal end of said lower piston rod therein, said piston rod having a distal end, in which said proximal ends of said respective cylinders are separated from each other by a longitudinal dimension in a range of about 20 to 30 centimeters. Further included is a lumbar cushion mounted upon an upper side of a rigid lumbar thrust surface, a lower side of said surface pivotally secured to each of said distal ends of said piston rods of said respective upper and lower cylinders; means for selectably changing the extent of extension of said upper piston rod relative to said upper cylinder; and means for selectably changing the extent of extension of said lower piston rod relative to said lower cylinder, whereby the height and angulation of said lumbar cushion relative to said body support frame may be readily changed by same assembly.

A principal object of the invention is to provide a multi-purpose table to effectuate flexion, extension, traction, lateral movement and distraction of the spine, as may be required in the treatment of spinal disorders and/or maintenance of proper human posture, in such a manner that the relative positions of the patient's arms, legs, lower back, head and shoulders can be varied.

Another object is to provide a multipurpose rotatable traction/treatment table permitting patient rotation and dynamic lifting of a patient while standing, concurrently with selective patient body positionings as may be required in the treatment of disc herniations and other disorders and/or maintenance of proper human posture.

Yet another object of the invention is to provide a treatment table having a range of motion from zero to at least ninety degrees and, within that range, which can pivot from zero to at least ninety degrees, thereby providing the ability to achieve spinal positioning including spinal flexion, extension, lateral flexion, and axial spinal positioning and traction in the absence of a lower leg support assembly enabled by inherent torso support and placement of the human body at or near its center of gravity at the lower back support assembly.

A still further object is to provide a table which having a variety of pneumatic and other adjustments to permit that patients of widely disparate age, height and weight to be accommodated, without requirement of extended physician set up time.

Another object of the invention is to provide a multi-purpose table that is simple to operate, weighted and designed for safety so as not to tip, and constructed of quality materials.

A yet further object is to provide a system in which the position of the upper torso support assembly may be varied relative to the lower back support assembly.

It is another object to provide a system than can concurrently or sequentially lift and/or rotate the patient, this providing various treatment options to the physician, including more effective and safer traction of vertebral segments by inducing less stress on atriculate vertebral surfaces of patient, and a generally more ergonomic patient interface.

A further obfect is to provide a system by which the patient may exercise and strengthen the spine and related musculature to maintain and enhance the health thereof.

It is another object to provide a treatment table capable of easy and variable patient means to remain on body support platform during "dynamic" liftoff including overhead or underarm patient hand gripping means and overhead thoracic harness strapping means.

It is a yet further object to effectuate flexion, extension, lateral flexion, and axial spinal positioning through easily accessed patient activated control switches to allow patient participation in treatment, improved patient safety, and better patient compliance.

Other objects and advantages of the invention will become apparent from the Detailed Description of the Invention, the Drawings, and Claims appended herewith.

BRIEF DESCRIPTION OF THE DRAWINGS

FIGS. 5–15 are views of different relative heights and angulations of a first cylinder-and-piston pair relative to a second pair, and resulting changes in position of the lumbar support cushion caused thereby.

DETAILED DESCRIPTION OF THE INVENTION

Figure 1:
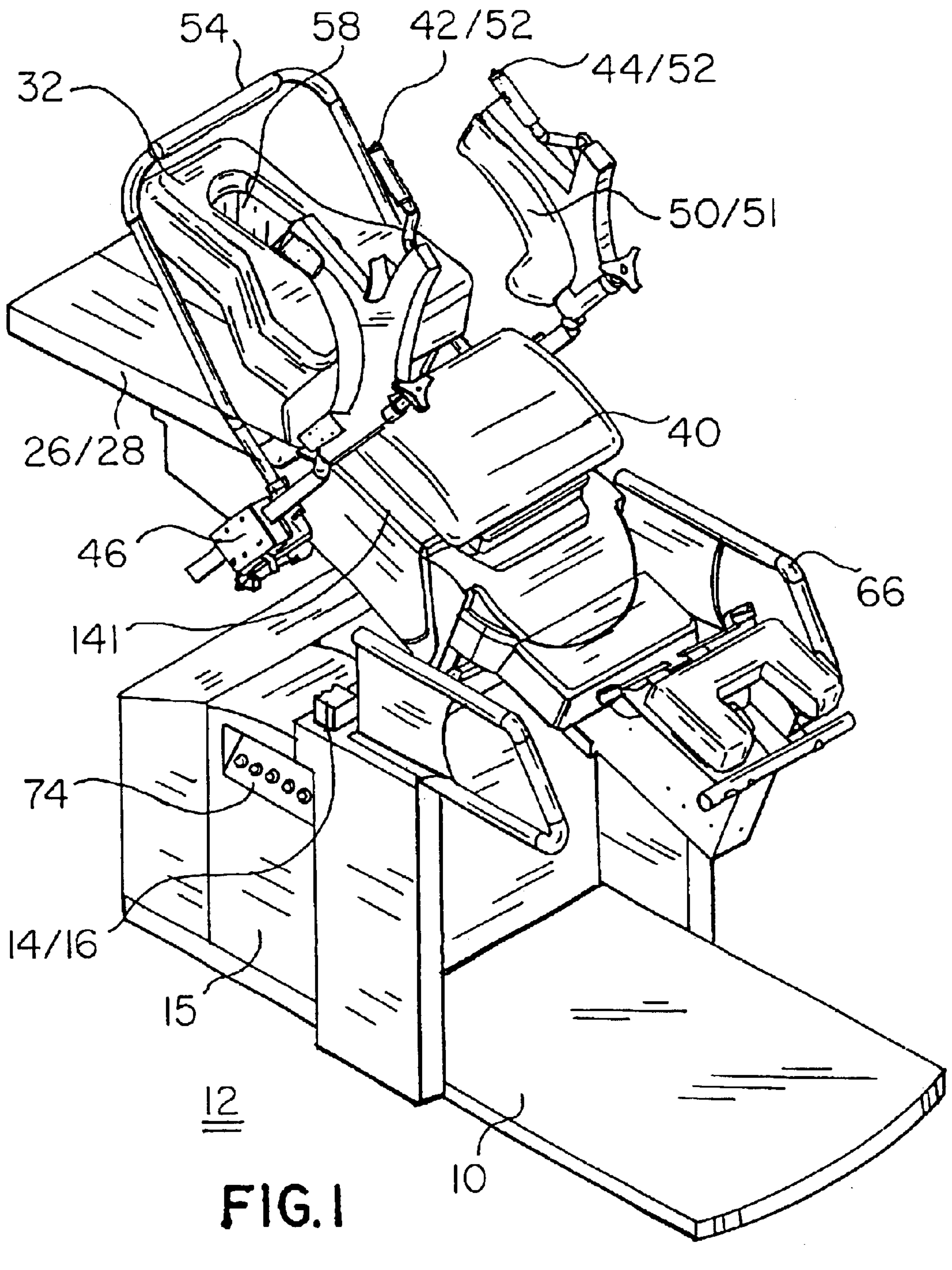
FIG. 1 is front diagonal perspective view of a chiropractic table which embodies the inventive lumbar support.
Figure 2:
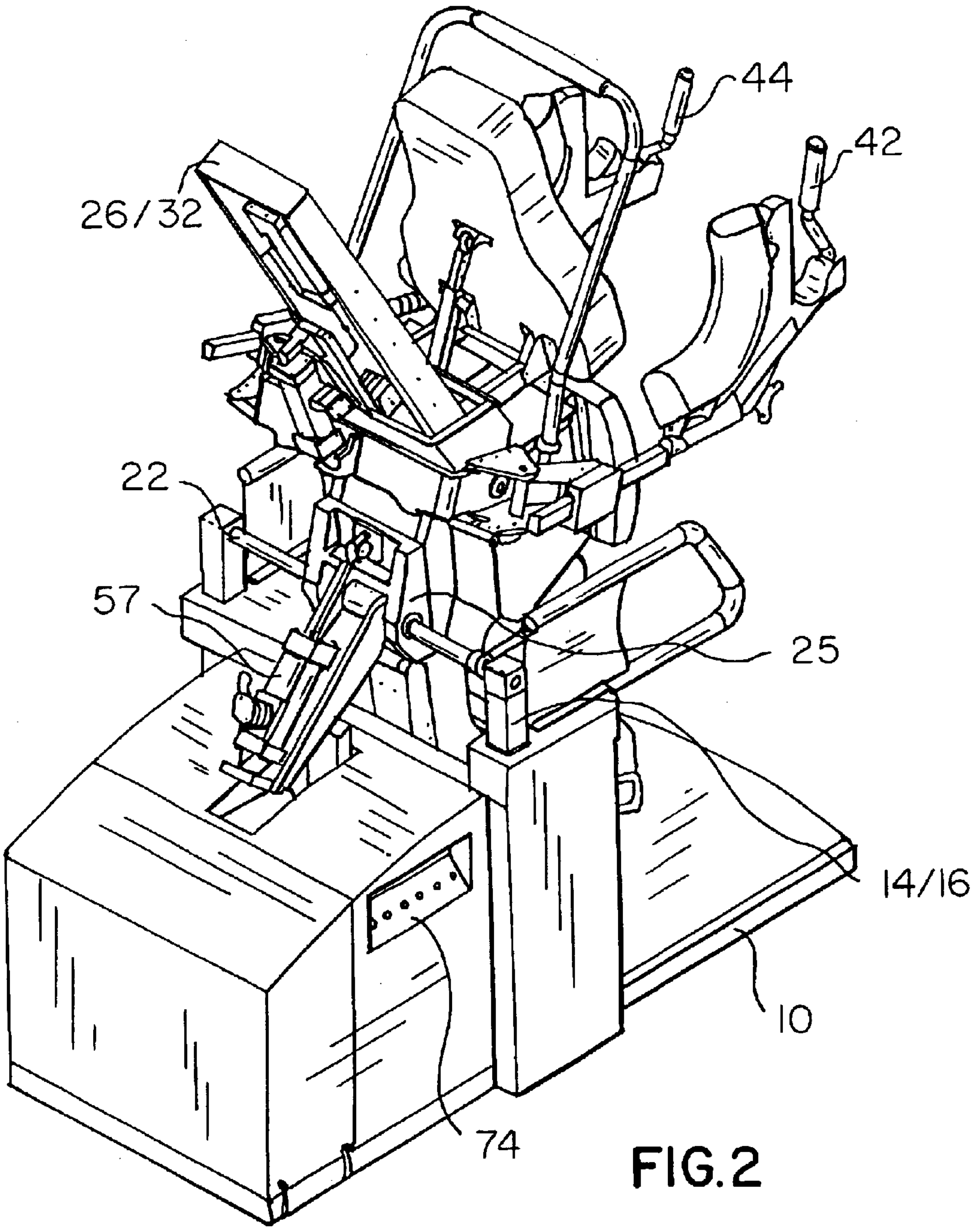
FIG. 2 is a rear diagonal perspective view of the structure of FIG. 1.

With reference to the views of FIGS. 1 and 2, the present chiropractic treatment table for effecting extension, flexion, traction and distraction of the spine of a patient, to which the invention relates, may be seen to include a base 10 adapted to rest upon a floor 12 in a typical treatment room of a chiropractor, physical therapist, or other health professionals involved in physical medicine. The chiropractic table may be seen to optionally include a pair of elevation means 14 and 16 to enable positioning of patients of various heights on the table. Elevation means 14 and 16 preferably comprise extensible hydraulic pistons, each including upper ends which support a transverse axle 22.

Figure 3:
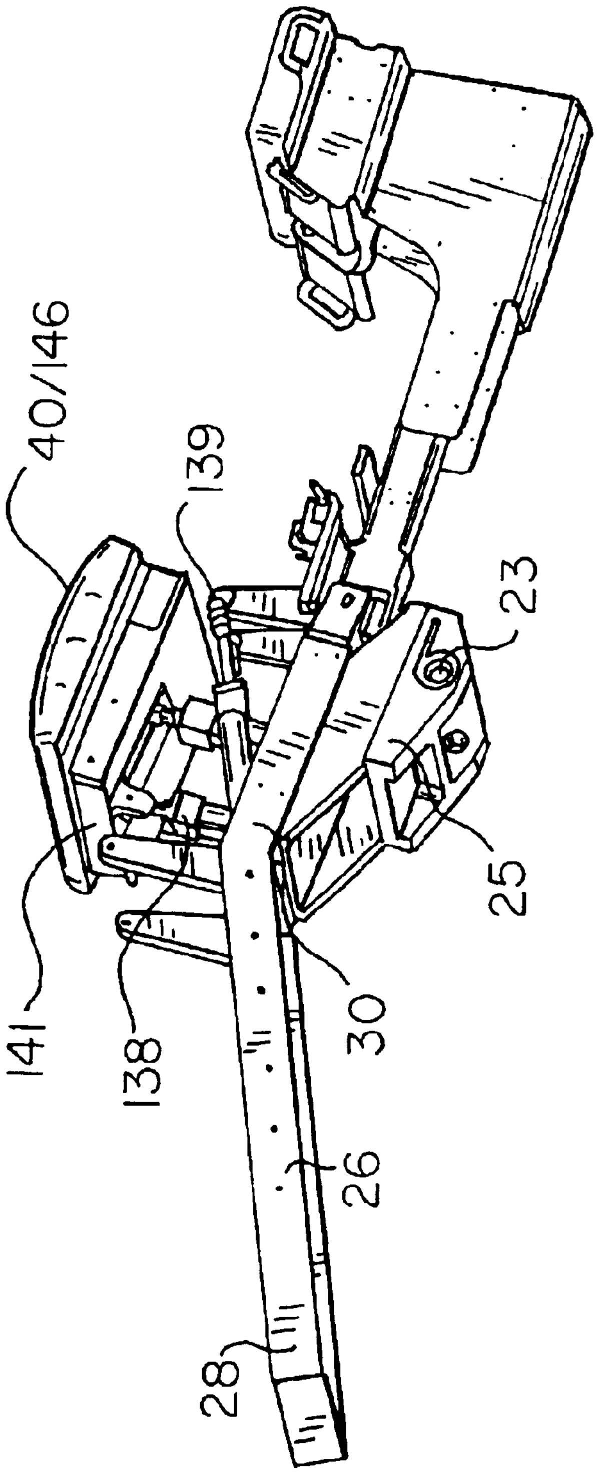
FIG. 3 is an elevational view of the lumbar back assembly.

As may be appreciated in the view of FIG. 3, axle 22 is journalled within channel 23 of block support 25 of rigid upper body support frame 26.

The instant multi-purpose treatment table thereby includes said upper support platform 26 having an upper part 28 and a lower part 30. Said lower part 30 of Upper rigid support frame or platform 26 is secured to said pivot block 25 (see FIG. 3) which is rotatable upon said pivot axle 22 at the approximate mid-point of lower part 30 of frame 26. As may be further noted, said upper part 28 defines a plane which is directed at an angle of about thirty degrees relative to a plane defined by said lower part 30 of the upper support platform 26. Such an angle is necessary in that it allows the patient's upper body to be ergonomically supported by a body support assembly 32, permitting the back to extend convexly and backward relative to base 10. Support assembly 32 is mounted upon said upper part 28 of said rigid support platform 26. Said body support assembly may or may not be divided into, and may or may not include, moveable sections with hydraulic or pneumatic pistons or other means for elevation and de-elevation of the body support assembly 32. Said assembly may contain an integral air bladder for additional immobilization.

With reference to FIGS. 1 and 2, the system may also be seen to optionally include a pair of positionally adjustable arm support means 42 and 44 which are located proximally to the sides of a body support assembly 32. As is set forth below, said arm support means include a selectably adjustable rear portion 46 which is secured to said upper part 28 of the rigid support platform 26. Said arm support means 42 and 44 include (i) substantially horizontal arm rests 50; (ii) a chest and shoulder support 51 situated posteriorly and angled inwardly in a patient direction from said arm rest; and (iii) a tilted hand grip 52 depending integrally upwardly and inwardly, proximally to said chest and shoulder supports 51.

The present treatment table may be seen to optionally include a lumbar and buttock support assembly 40, which is displaced from said body support assembly 32. Lumbar assembly 40 is connected to telescoping piston rods 53 and 55 (see FIG. 4) or other means which provide for elevation and de-elevation thereof. Said assembly may include an internal air cushion in the form of an inflatable air bladder, for added support and tissue mobilization. The same is true of the upper torso support assembly.

Figure 4:
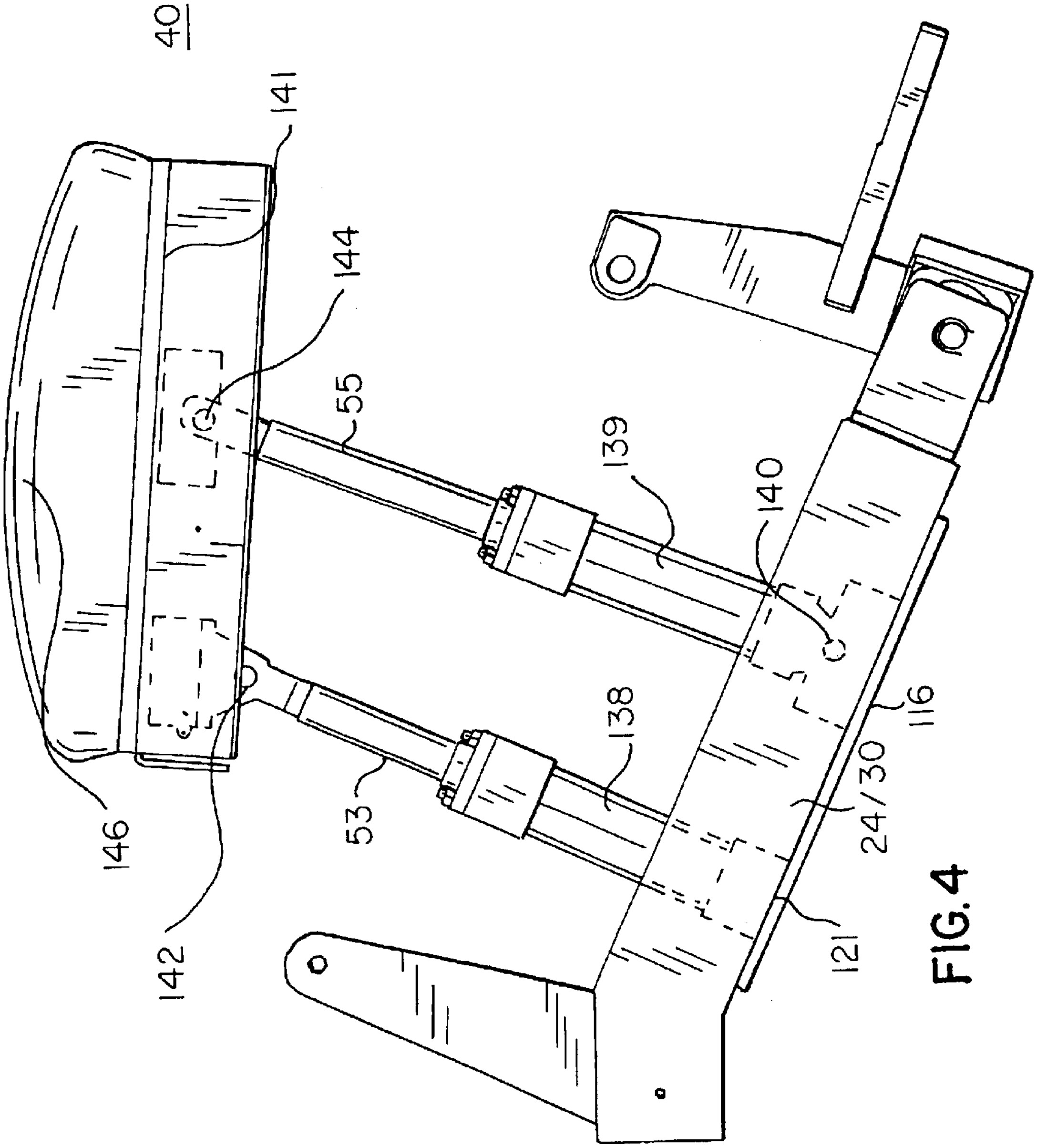
FIG. 4 is a side operational view of the lumbar support assembly in which a lower piston rod thereof is extended to greater extent than an upper piston rod.
Figure 5:
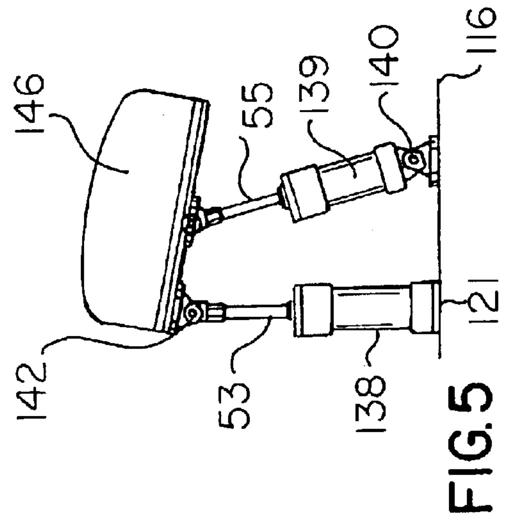
Figure 6:
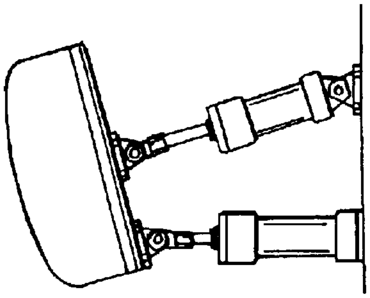
Figure 7:
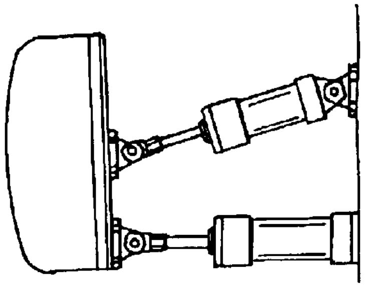
Figure 8:
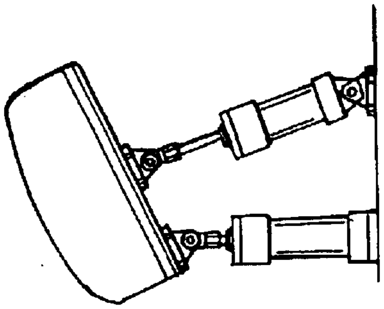

More particularly, shown in FIG. 4 is the use of airfoil pistons 138 and 139, both of which are secured, at the proximal ends thereof, to a rigid support plate 116 that is secured to lower part 30 of rigid support platform 26. It is, however, to be noted that lower airfoil piston 139 is pivotally secured to support plate 116 at a pivot point 140, while upper airfoil piston 138 is rigidly secured to plate 116 at point 121. Distal ends of piston rods 53 and 55 are both pivotally attached to rigid lumbar thrust plate 141 at points 142 and 144 respectively. As such, lumbar support cushion 146 may be readily tilted relative to platform 26 to provide independent articulation, movement, and adjustment of the effective radius of cushion 146, that is, relative to lower portion 30 of platform 26 as is shown in FIGS. 5 thru 16.

Therein may be seen the essentially unlimited number of variations of height and angulations of the lumbar assembly that may be achieved by the present system.

The present chiropractic table may be seen to further include means for selectable reciprocal vertical extension, i.e., an electromechanical linear actuator or an extensible hydraulic or pneumatic piston 57 (see FIG. 2) which enables rotation of said rigid support platform 26, upon said horizontal pivot axle 22, by rotation of pivot block 25 to which platform 26 is secured. It is, accordingly, to be appreciated that extensible piston 57 facilitates a central function of the chiropractic table, i.e., the rotation of all assemblies attached to the rigid support platform 26, including body support assembly 32, the lumbar support assembly 40, and the adjustable arm support means 42, all through the use of a single control means, namely, extensible piston 57.

Figure 16:
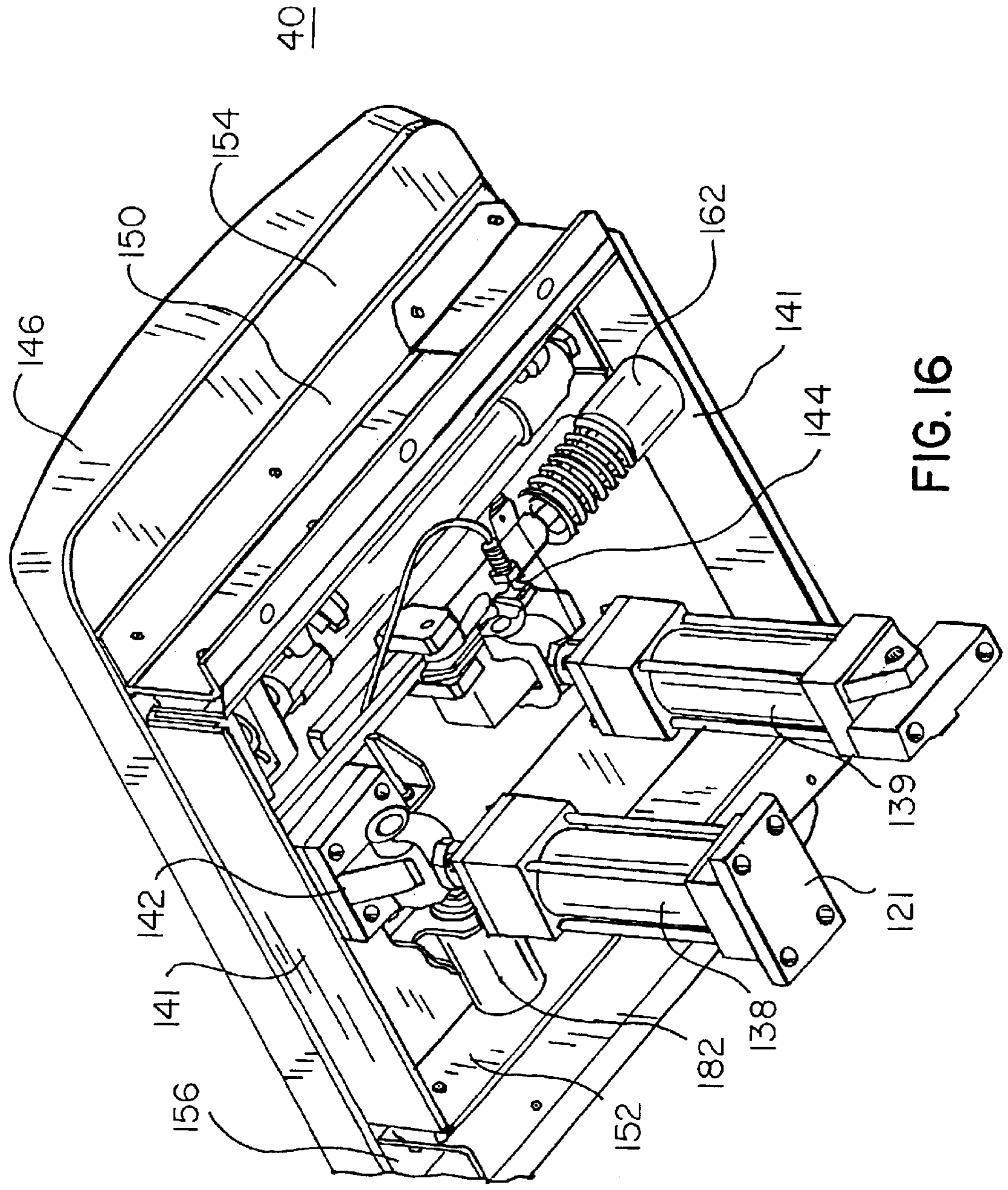
FIG. 16 is a bottom-up view of the lumbar traction assembly.

With reference to the bottom-up view of FIG. 16 of the lumbar traction assembly 40, the lumbar bottom cover is removed to reveal the components of the assembly inside of the lumbar that plate 116. The lumbar support frame and support frame plate are also removed to facilitate the illustration of FIG. 16. As may be noted, the lumbar side brackets 150/156 are slidably mounted to lumbar plate 116. Therein, said plate 116, a lumbar cushion plate 154, and lumbar cushion 146 are rigidly mounted on lumbar side brackets 150/156 of lumbar traction assembly 40 may thereby move lumbar cushion 146 relative to lumbar support plate 116.

Figure 17:
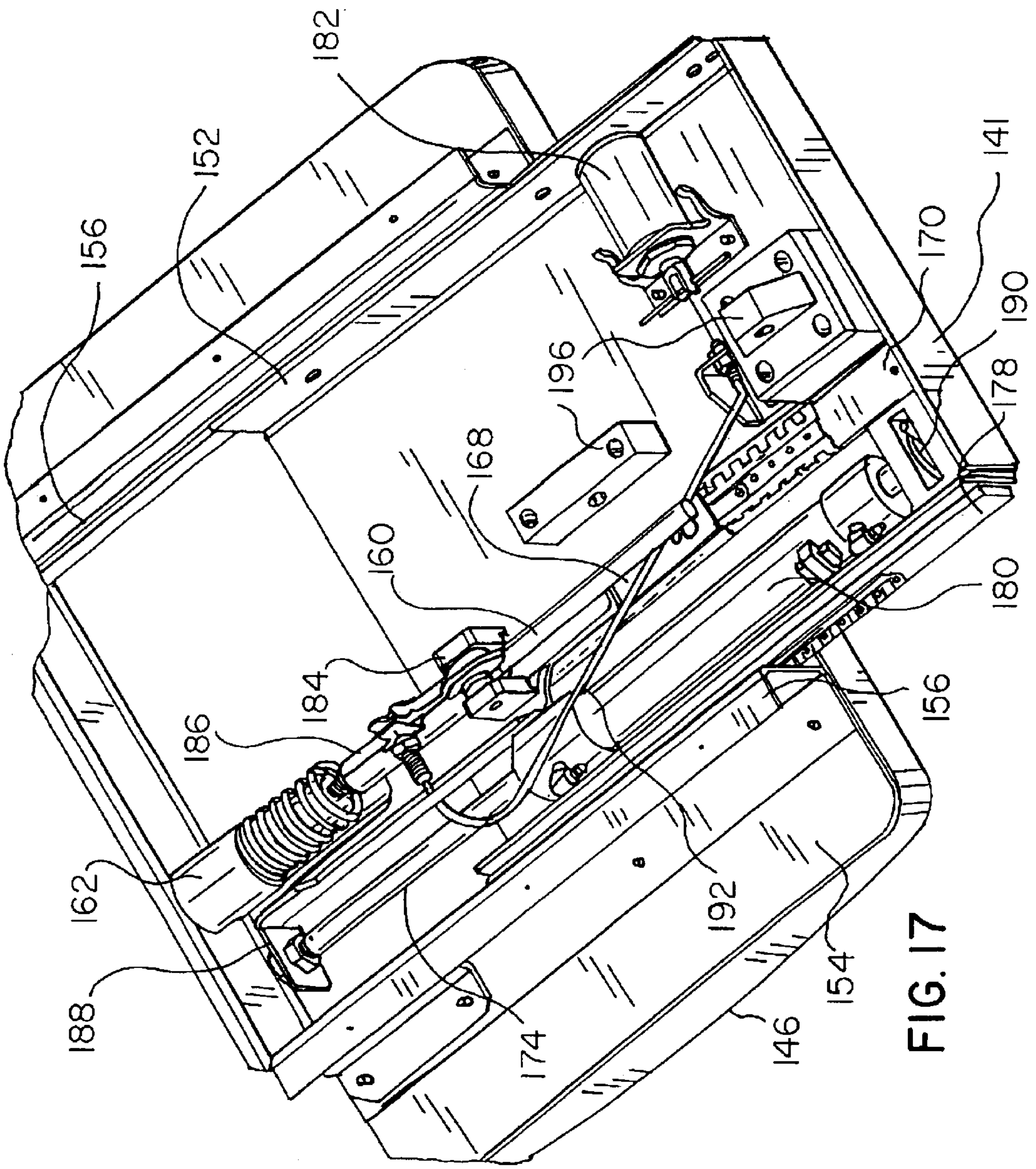
FIG. 17 is an upside down view thereof.
Figure 18:
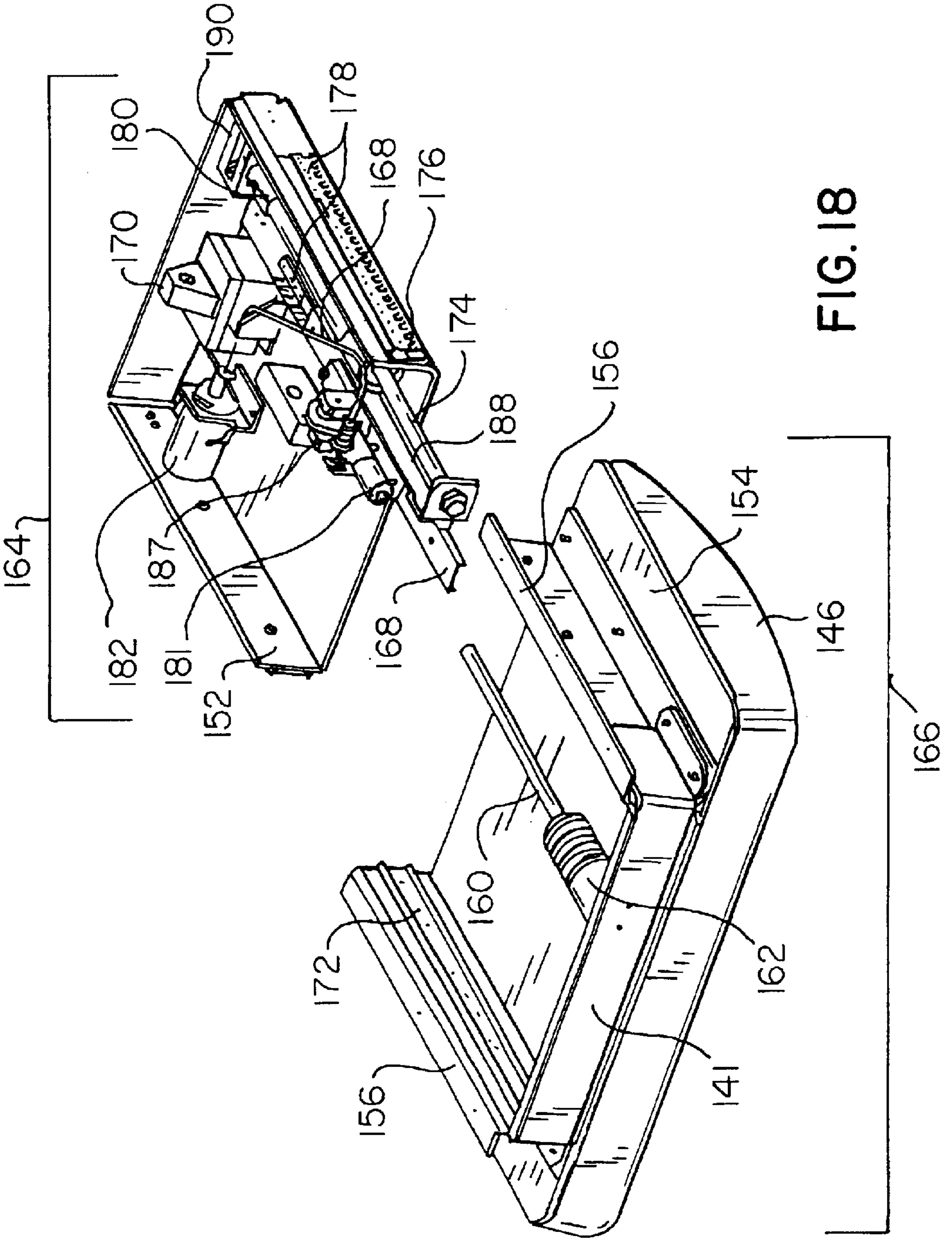
FIG. 18 is an exploded view of the major mechanical groups of the lumbar traction assembly.

With reference to FIGS. 17 and 18, shown a top view of the assembly of FIG. 16 which, particularly, illustrates the process of power traction of the inventive lumbar support and adjustment assembly. Therein, a mechanical lock rod 160 screws onto a spring assembly 162 which is fixed onto a lumbar thrust bracket 141. Said thrust bracket is, in turn, attached to lumbar side brackets 150/156 on which the lumbar cushion 146 and lumbar cushion plate 154 are mounted. A lumbar cushion group 166 thus formed is slidably mounted to the other components of the lumbar plate group 164. Thereafter, lumbar cushion group 166 is locked onto a mechanical lock slide 168 for linear movement, sliding into lumbar plate center slide 170. In addition to plate center slide 170, the lumbar cushion group 166 is also slidably mounted at the sides of the lumbar cushion plate 154 by a pair of lumbar side bracket slides 172.

Further shown in FIGS. 17 and 18 are lumbar traction hydraulic rod 174, lumbar plate side slide 176, ball bearing sleeve assembly 178, lumbar traction hydraulics 180, mechanical lock solenoid 182, mechanical lock clamp 184, lumbar mechanical lock 186, link bracket 188, load cell 190, mechanical lock release table 192, lumbar plate side slide 194, and up and down lumbar mounting plates 196.

The above described lumbar plate group 164 and lumbar cushion group 166 the power traction function of the inventive multi-function chiropractic treatment table. That is, after the proper height and angulation of the lumbar support and adjustment assembly, shown in FIGS. 4–15, has been established, the doctor may, through the use of controls 74 (see FIGS. 1 and 2) accomplish selective stretching or traction of the lower back of the patients while handles 42 and 44 are held.

FIGS. 1 and 2 further illustrates a system control 74 for use by the doctor which includes the following functions buttons:

| | | |
|---|---|---|
| 1. | TBL LFT = | Table Lift. |
| 2. | TBL LWR = | Table Lower. |
| 3. | ROT BACK = | Rotate Table Back. |
| 4. | ROT FWD = | Rotate Table Forward. |
| 5. | ARM UP = | Translational Arm Height Up. |
| 6. | ARM DWN = | Translational Arm Height Down. |
| 7. | OPEN | |
| 8. | OPEN | |
| 9. | ARM R. UP = | Arm Rotate Up. |
| 10. | ARM R. DOWN = | Arm Rotate Down. |
| 11. | LUM IN = | Lumbar In |
| 12. | LUM OUT = | Lumbar Out |
| 13. | OPEN | |
| 14. | OPEN | |
| 15. | RBK TL = | Rotate Table Back with Table Lift. |
| 16. | RFW TLW = | Rotate Table Forward with Table and Lower Table. |
| 17. | SAFETY ON AND OFF = | A safety on and off button is included which stops pneumatic/hydraulic piston and ceases all table movement. |

As a safety measure, controls may also be incorporated into overhead gripping means 54 or into handgrips 42 (see FIGS. 1 and 2), with optional patient control of other functions.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention.

Having described my invention, what I claim as new, useful and non-obvious and, accordingly, secure by Letters Patent of the United States is:

1. A multi-function chiropractic treatment table having a lumbar support and adjustment assembly comprising:

(a) a lumbar support plate mounted upon a rigid body support frame of said table;

(b) an upper pneumatic cylinder having an upper piston rod associated therewith, said cylinder having a proximal end rigidly secured to said support frame and having a distal end having an aperture for fluid tight reciprocal receipt of a proximal end of said piston rod therein, said piston rod also having a distal end;

(c) a lower pneumatic cylinder having a lower piston rod associated therewith, said lower cylinder having a proximal end pivotally secured to said support frame and having a distal end having an aperture for fluid tight reciprocal receipt of a proximal end of said lower piston rod therein, said piston rod having a distal end, in which said proximal ends of said respective cylinders are separated from each other by a longitudinal dimension in a range of about 20 to 30 centimeters;

(d) a lumbar cushion mounted upon an upper side of a rigid lumbar cushion plate, a lower side of said rigid lumbar cushion plate pivotally secured to each of said distal ends of said piston rods of said respective upper and lower cylinders;

(e) means for selectably changing the extent of extension of said upper piston rod relative to said upper cylinder; and (f) means for selectably changing the extent of extension of said lower piston rod relative to said lower cylinder, whereby the height and angulation's of said lumbar cushion relative to said body support frame may be readily changed by same assembly.

2. The assembly as recited in claim 1 in which:

(g) said lumbar support assembly is displaced from said rigid body support frame; and (h) said upper and lower cylinders and their respective piston rod comprise means for independent articulation of said lumbar assembly in a plane either above, or tilted, relative to opposing portions of said body support frame.

3. The assembly as recited in claim 1, further comprising:

a lumbar thrust plate, and a means for selectably sliding said lumbar thrust plate on said body support frame to thereby produce traction upon the body of a patient.

* * * * *